United States Patent [19]

Hinzmann

[11] Patent Number: 4,755,164

[45] Date of Patent: Jul. 5, 1988

[54] METHOD OF AND APPARATUS FOR MAKING APPLICATORS OF PLEDGETS AND THE LIKE

[75] Inventor: Alfred Hinzmann, Weems, Va.

[73] Assignee: Hauni Richmond, Inc., Richmond, Va.

[21] Appl. No.: 945,774

[22] Filed: Dec. 23, 1986

[51] Int. Cl.$^4$ .................... B31B 1/16; B31B 1/60; B65H 54/00

[52] U.S. Cl. .................... 493/288; 493/156; 493/158; 493/297; 493/352; 493/960; 156/201; 156/203; 156/256; 156/466; 156/522

[58] Field of Search .............. 156/201, 203, 256, 270, 156/466, 522; 493/45, 156, 158, 217, 223, 224, 230, 238, 239, 276, 277, 278, 287, 288, 290, 297, 302, 308, 352, 363, 945, 960

[56] References Cited

U.S. PATENT DOCUMENTS

| | | | |
|---|---|---|---|
| 1,006,976 | 10/1911 | Osborn | 493/297 |
| 3,094,083 | 6/1963 | Weeks | 493/217 |
| 3,518,911 | 7/1970 | Niemann et al. | 83/338 |
| 3,683,759 | 8/1972 | Voss et al. | 493/231 |
| 4,063,480 | 12/1977 | Hinzmann | 83/176 |
| 4,154,090 | 5/1979 | Heitmann et al. | 73/38 |
| 4,302,174 | 11/1981 | Hinzmann | 425/341 |
| 4,321,993 | 3/1982 | Hinzmann et al. | 198/400 |
| 4,353,454 | 10/1982 | Tolasch et al. | 198/347 |
| 4,365,702 | 12/1982 | Tolasch et al. | 198/347 |
| 4,412,833 | 11/1983 | Wiegner et al. | 604/14 |
| 4,423,742 | 1/1984 | Reuland | 131/84 C |
| 4,453,925 | 6/1984 | Decker | 604/14 |
| 4,485,826 | 12/1984 | Holzangel | 131/84 C |
| 4,508,531 | 4/1985 | Whitehead | 604/14 |
| 4,580,579 | 4/1986 | Wahle et al. | 131/84.3 |

FOREIGN PATENT DOCUMENTS 0115193 8/1984 European Pat. Off. .

Primary Examiner—Frederick R. Schmidt
Assistant Examiner—William E. Terrell
Attorney, Agent, or Firm—Peter K. Kontler

[57] ABSTRACT

An applicator for tampons has a sleeve for the tampon and for a portion of a reciprocable pusher which can expel the tampon by causing the latter to flex outwardly a set of domed petals at the front end of the sleeve. The sleeve is formed by advancing a strip of degradable material longitudinally, by forming spaced-apart portions of the strip with transversely extending rows of hourglass-shaped webs, by converting the strip into a tubular envelope with a seam extending in parallelism with the axis of the envelope, by severing the envelope across the rows of webs so that the envelope yields a series of tubes each having a circumferentially extending set of petals (halves of webs) at each of its ends, and by cutting each tube midway between its ends to form shorter tubes (sleeves) each of which has a set of petals at one end. The petals are thereupon domed to close the respective ends of the sleeves and the other ends of the sleeves are formed with indentations which center the respective pushers. The strip can be assembled with a row of tubular reinforcing members which are placed between successive rows of webs and are confined in the envelope. Each sleeve then contains an inner tubular component which constitutes one-half of a reinforcing member and an outer tubular component which constitutes one-half of a tube and has petals extending beyond one end of the inner tubular component.

20 Claims, 4 Drawing Sheets

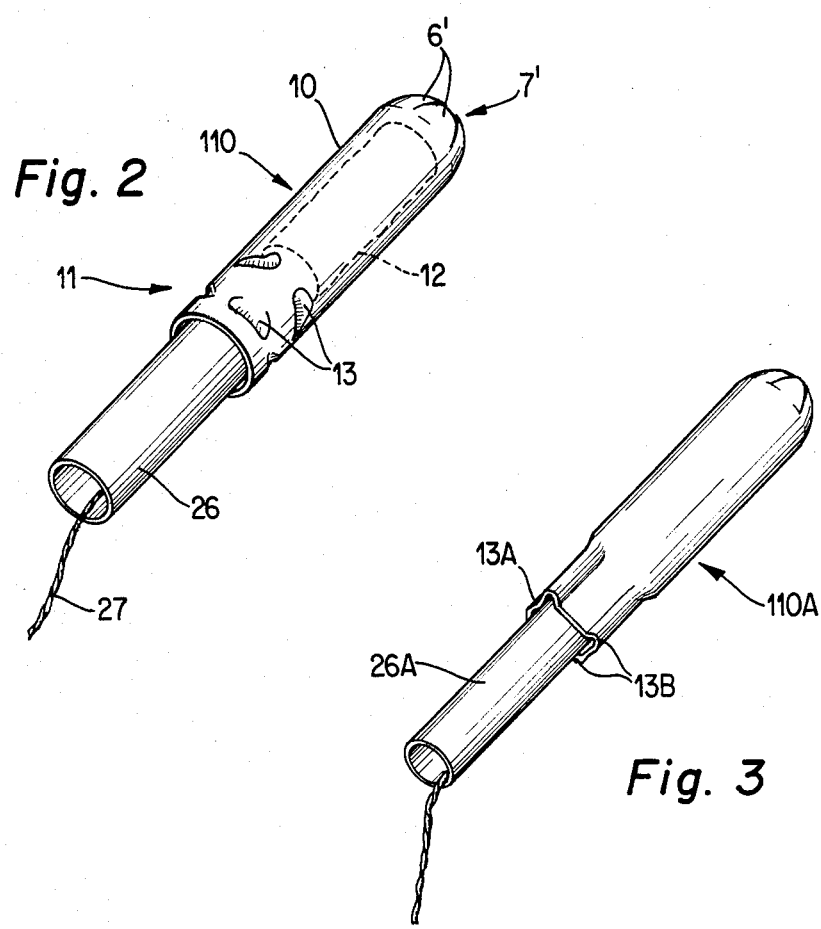
Fig. 2
Fig. 3
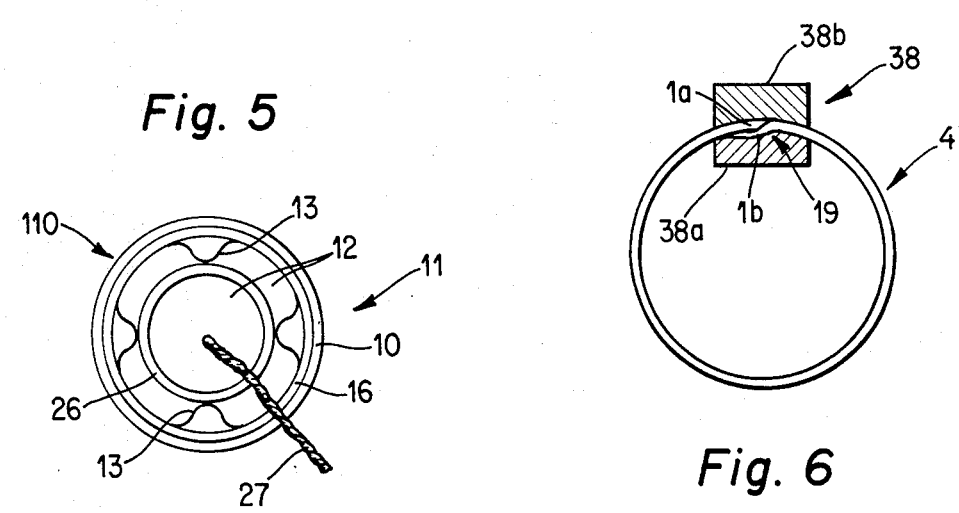
Fig. 5
Fig. 6

METHOD OF AND APPARATUS FOR MAKING APPLICATORS OF PLEDGETS AND THE LIKE

BACKGROUND OF THE INVENTION

The invention relates to a method of and to an apparatus for making applicators of pledgets and like objects. More particularly, the invention relates to improvements in methods of and in apparatus for making applicators which can be used for insertion of catamenial tampon pledgets. The invention also relates to applicators and parts of applicators which are produced in the improved apparatus by resorting to the improved method.

The following description will deal exclusively, or practically exclusively, with the making of applicators for catamenial tampon pledgets. However, such method and apparatus can be used with equal or similar advantage for the making of applicators or holders of other types of objects, for example, firecrackers.

Commonly owned U.S. Pat. Nos. 4,302,174 to Hinzmann and 4,321,993 to Hinzmann et al. disclose tampon applicators of the type wherein a plastic shell is formed with domed petals at one of its ends and its other end receives a pusher. The pusher is or can be hollow to provide room for a pull thread or cord attached to a pledget which is confined in the shell between the domed petals and the front end of the pusher. These applicators operate satisfactorily and are in widespread use. However, the plastic material of shells and pushers is not soluble in water, e.g., in a body of water in a toilet bowl, so that the disposal of spent applicators presents serious problems. Spent applicators can be found in waste baskets, on streets and on beaches.

In accordance with several prior proposals, the applicators of pledgets are to be made of degradable material which readily disintegrates in water so that a spent applicator can be dropped into and flushed from the bowl of a toilet. The dissolution is rapid and complete so that the applicator is not likely to clog the waste evacuating pipes of toilets. Such prior proposals are disclosed, for example, in U.S. Pat. Nos. 4,412,833 to Wiegner et al. and in 4,453,925 to Decker. A drawback of the patented applicators is that the shells are made from helically convoluted strip stock with helically extending seams. The pushers of these applicators constitute tubes which are made in the same way as the shells, i.e., by winding one or more strips of cardboard or the like around a suitable mandrel and by advancing the thus obtained cylindrical envelope axially to a severing station where the envelope is subdivided into pushers or shells of desired length. One end of each shell is thereupon provided with notches alternating with so-called petals which are domed inwardly in a nextfollowing operation to form a crown which partly or fully closes the respective end of the shell in order to facilitate insertion of the shell into the body cavity prior to expulsion of the pledget by the pusher. The expulsion involves pushing the pledget against the domed petals so that the petals are flexed outwardly and provide an opening for the pledget.

A drawback of the just described applicators is their high cost which is due to the fact that the output of apparatus for making the applicators is very low. Thus, it is necessary to convert one or more strips into a first tubular envelope which is subdivided into discrete pushers, to convert one or more strips into a second tubular envelope which is converted into shells, to provide one end of each discrete shell with a set of cutouts and to dome the thus obtained petals prior to insertion of a pledget and a pusher. Moreover, it is very difficult or plain impossible to make clean cuts (notches) in the end faces of shells which are made by helically winding one or more strips of cardboard or other degradable material because fragments of such material tend to become separated from the petals and then remain in the body cavity of the user of the pledget and cause discomfort and/or infection.

U.S. Pat. No. 4,508,531 to Whitehead discusses the drawbacks of conventional spirally wound shells for use in applicators of pledgets and proposes to make the petals on blanks which are thereupon converted into shells by so-called convolute winding which apparently involves rolling the blank around a suitable mandrel. The cost of making such applicators is still very high since the apparatus which makes convolutely wound shells must receive a supply of prefabricated blanks each of which has a row of petals along one of its edges. A similar proposal is disclosed in the published European patent application Ser. No. 0,115,193.

OBJECTS AND SUMMARY OF THE INVENTION

An object of the invention is to provide a novel and improved method of making portions of and entire applicators of pledgets or the like.

Another object of the invention is to provide a method which renders it possible to turn out portions of and entire applicators at a rate (e.g., 600 per minute) several times that achievable in accordance with heretofore known methods.

A further object of the invention is to provide a novel and improved method of making shells for the pledgets of tampon applicators.

An additional object of the invention is to provide a novel and improved applicator of pledgets and the like.

A further object of the invention is to provide a novel and improved shell for the pledget of the above outlined applicator.

An additional object of the invention is to provide a novel and improved combination of shells and pushers for use in the above outlined applicators.

Still another object of the invention is to provide an applicator which can be readily and reliably grasped by hand and wherein the pusher is reliably held in the shell in a selected position but can be shifted relative to the shell in response to the exertion of a relatively small expulsion force.

Another object of the invention is to provide the shell with novel and improved means for holding the pusher in an optimum position.

A further object of the invention is to provide a readily disposable applicator which can be made from a wide variety of known materials capable of disintegrating in water and being flushable practically immediately after entering the bowl of a toilet.

Another object of the invention is to provide a novel and improved apparatus for the practice of the above outlined method and for the making of the above outlined applicator.

Still another object of the invention is to provide the apparatus with novel and improved means for making the shell of the applicator and with novel and improved means for making the pusher.

A further object of the invention is to provide an apparatus which can operate properly at a full speed or at a reduced speed even if one or more of its constituents are out of commission for relatively long periods of time.

Another object of the invention is to provide the apparatus with novel and improved means for properly positioning the pusher in the shell of the applicator and with novel and improved means for facilitating manipulation of the shell.

An additional object of the invention is to provide the apparatus with novel and improved means for making shells which are sufficiently sturdy to allow for reliable confinement of pledgets therein but whose petals are readily deformable to allow for expulsion of pledgets in response to the exertion of a relatively small force.

A further object of the invention is to provide a novel and improved maker of shells with petals for use in applicators of catamenial tampon pledgets or the like.

One feature of the invention resides in the provision of an applicator of catamenial tampon pledgets or other objects which comprises a sleeve having a first end and a second end. The first end has a set of circumferentially extending domed petals which together form a substantially bullet-shaped hollow crown having a substantially convex or frustoconical outer side. The sleeve includes a converted sheet of degradable material with two substantially parallel marginal portions overlapping each other and being bonded to one another to form a seam which extends in substantial parallelism with the axis of the sleeve. The applicator further comprises a pusher which extends through the second end and into the interior of the sleeve and is in frictional engagement with the sleeve.

The sleeve can be provided with a plurality of inwardly extending centering indentations in the region of the second end. The indentations center and are in frictional engagement with the inserted portion of the pusher. The depth of the indentations (as measured radially of the sleeve) is preferably such that the inner diameter of the sleeve appreciably exceeds the outer diameter of the pusher. By way of example, the inner diameter of the sleeve can exceed the outer diameter of the pusher by 50-100 percent. The pusher is or can constitute a tubular body with open ends. The indentations ensure that only a small portion of the external surface of the pusher is in actual contact with the sleeve.

The sleeve is preferably formed with an uneven external surface, at least in the region of its second end, so as to facilitate grasping of the sleeve during shifting of the pusher in a direction toward the first end of the sleeve.

The sleeve can comprise an inner tubular component and an outer tubular component which surrounds the inner component. The petals are provided at one end of the outer component and extend beyond the respective end of the inner component.

Another feature of the invention resides in the provision of a sleeve which can be used in the above described applicator and has a set of petals at one axial end and a seam which extends in parallelism with its axis. The shell can comprise the aforementioned inner tubular component and the aforementioned outer tubular component which is provided with petals.

A further feature of the invention resides in the provision of a twin sleeve (hereinafter called tube) which has a set of petals at each of its ends and a seam which extends in parallelism with its axis. The tube can be severed to yield two discrete sleeves. Doming of the petals and the insertion of pledgets into the sleeves can be carried out at a location other than the locus of making the sleeve, the tube and/or the pusher. For example, the tubes and the pushers can be made in a first plant and can be transported to another plant where they are assembled with one another and with pledgets to constitute finished applicators. Alternatively, the entire applicators can be assembled in a single apparatus which has a maker of pushers, a maker of tubes, and a maker or assembler of applicators. The assembler can include a unit which forms pledgets, or such assembler can receive prefabricated pledgets from another apparatus or from another plant.

The number of petals in each set is preferably the same and the number of petals in a set can exceed four.

Still another feature of the invention resides in the provision of a method of making tubes, particularly for use in applicators of catamenial tampon pledgets. The method comprises the steps of establishing and maintaining a source of supply of a strip of degradable material, conveying the strip longitudinally along a predetermined path, removing material from longitudinally spaced-apart portions of the running strip in a first portion of the path so as to form transversely extending rows or groups of substantially hourglass-shaped webs, converting the strip into a tubular envelope in a second portion of the path, and severing the envelope substantially midway across the rows of webs in a third portion of the path so as to subdivide the envelope into a series of tubes having ends formed by circumferentially extending sets of petals. Each petal can constitute substantially one-half of a web.

The method can further comprise the step of cutting each tube substantially midway between its ends to form pairs of tubular sections each having a set of petals at one of its ends.

The method can further comprise the step of storing at least some of the tubes or tubular sections in at least one reservoir, for example, in a first-in last-out reservoir (such reservoir can store up to and in excess of 10,000 tubes or tubular sections).

Each tubular section can be provided with inwardly extending indentations in the region of the other end of the respective tubular section, i.e., in the region which is remote from the petals. The petals are domed in a further step so that they jointly form a hollow bullet or crown which closes or partly closes the respective end of the tubular section.

The method can further comprise the steps of juxtaposing successive tubular reinforcing members with the strip so that each reinforcing member is located between two successive rows of webs not later than upon arrival of the webs into the second portion of the path so that the reinforcing members are confined in the envelope in the course of the converting step. Such method further comprises the step of cutting the tubes and the respective reinforcing members midway between their ends so that the tubes and the respective reinforcing members jointly yield pairs of twin-walled sleeves or shells each having an inner tubular component constituting substantially one-half of the respective reinforcing member and an outer tubular component constituting substantially one-half of the respective tube and having a set of petals at one of its ends. The petals extend beyond the respective end of the inner component. At least some of the sleeves can be stored, e.g., in a first-in last-out reservoir.

The converting step preferably comprises applying a film of adhesive to at least one longitudinally extending marginal portion of the strip and bonding the one marginal portion to the other longitudinally extending marginal portion of the strip so that the two marginal portions form a seam extending in substantial parallelism with the axis of the resulting envelope. Such method can further comprise the step of ironing the seam so as to provide a smooth transition between the exposed side of the outer marginal portion of the seam (e.g., the one marginal portion) into the outer side of the adjacent longitudinally extending portion of the envelope.

The degradable material is or can be selected from the group consisting of paper, board, cardboard and paperboard.

The pushers can be formed in the same way as the tubes except that the strip which is converted into an envelope consisting of coherent pushers need not be provided with cutouts and webs. The same applies for the making of tubular reinforcing members.

A presently preferred embodiment of apparatus for the practice of the above outlined method comprises a source of supply (e.g., a reel or bobbin and the mounting means therefor) of a continuous strip of degradable material, means (e.g., a system of driven rolls) for advancing the strip from the source longitudinally along a predetermined path, means for removing material from longitudinally spaced-apart portions of the running strip in a first portion of the path in order to form substantially transversely extending rows of substantially hourglass-shaped webs, means for converting the strip into a tubular envelope in a second portion of the path, and means for severing the envelope substantially midway across successive rows of webs so as to subdivide the envelope into a series of tubes each of which has both ends formed by circumferentially extending sets of substantially triangular petals each constituting approximately one-half of a web. The converting means can comprise means for applying adhesive to at least one longitudinally extending marginal portion of the strip and means for bonding the one marginal portion to the other longitudinally extending marginal portion of the strip so as to form a seam which extends in substantial parallelism with the axis of the envelope. The converting means can further comprise means for ironing the seam so as to provide a smooth transition between the exposed side of the outer marginal portion of the seam and the outer side of the adjacent longitudinally extending portion of the envelope.

The apparatus further comprises means for cutting the tubes substantially midway between their ends so that each tube yields two tubular sections each having a set of petals at one of its ends.

The apparatus can further comprise a source (e.g., a maker) of tubular reinforcing members and means for juxtaposing discrete reinforcing members with the strip between the source of supply of the strip and the converting means in such distribution that each reinforcing member is disposed between two consecutive rows of webs (as seen in the longitudinal direction of the strip) and the reinforcing members are confined in the envelope which is formed by the converting means so that each tube contains a reinforcing member and the sets of petals on each tube extend axially of the tube beyond the respective ends of the reinforcing member in the tube. The cutting means then severs each tube and the reinforcing member in the tube substantially midway between the axis ends of the tube to form twin-walled sleeves or shells each having an inner tubular component constituting substantially one-half of the respective tubular reinforcing member and an outer tubular component constituting substantially one-half of the respective tube and having a set of petals at one of its ends, with the petals extending beyond the respective end of the inner component.

As mentioned above, the source of reinforcing members can include or constitute a maker of reinforcing members, and such apparatus can further comprise means (e.g., a duct) for transferring reinforcing members from the maker to the juxtaposing means, and a reservoir (e.g., a first-in last-out reservoir) which communicates or cooperates with the transferring means to receive the surplus of reinforcing members when the maker supplies reinforcing members at a rate exceeding the requirements of the juxtaposing means and to supply reinforcing members to the transferring means when the requirements of the juxtaposing means exceed the output of the maker.

The apparatus can further comprise means for inserting pledgets into the sections of tubes (or into the aforementioned sleeves if each section contains one-half of a reinforcing member), and means (e.g., a duct or chute or a system of rollers) for transferring sections from the cutting means (where the tubes are halved) to the inserting means.

A reservoir (e.g., a first-in last-out reservoir) can be combined with the means for transferring or transporting tubes or sections of tubes from the severing means toward the inserting means, and such reservoir is designed to receive the surplus of tubes o sections when the output of the tube maker or section maker exceeds the requirements of the inserting means, and to supply tubes or sections to the transporting means when the requirements of the inserting means exceed the output of the maker including the severing means.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 2 is a perspective view of a fully assembled applicator with a pledget in the interior of its shell;

FIG. 3 is a perspective view of a modified applicator;

FIG. 5 is an enlarged rear end view of the applicator of FIG. 2;

FIG. 6 shows the means for ironing the seam of the envelope which is converted into the outer tubular components of sleeves.

DESCRIPTION OF THE PREFERRED EMBODIMENTS

Figure 1:
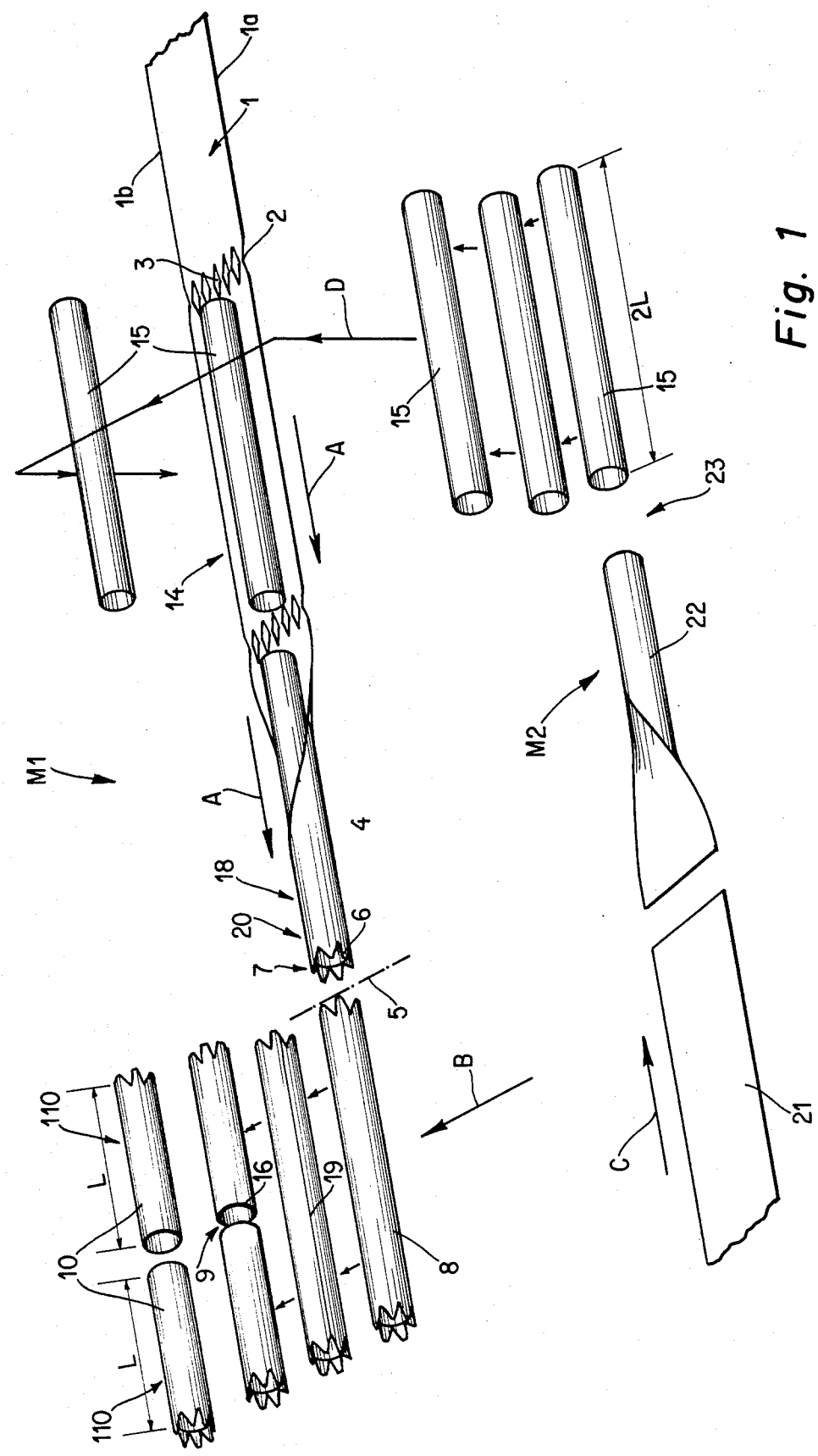
FIG. 1 is a diagram showing the manner of converting two strips of degradable material into a series of shells each of which has an inner tubular component and an outer tubular component with a set of petals.

The method of making twin-walled sleeves or shells 110 (FIGS. 1 and 2) of applicators 11 or 11A of catamenial tampon pledgets 12 (hereinafter called tampons for short) will be described with reference to FIGS. 1 to 4.

A maker M1 of sleeves 110 comprises a reel or bobbin 24 constituting a source of supply of a continuous deformable strip 1 which is preferably degradable (i.e., it decomposes in water) and can consist of or contain paper, board, paperboard or cardboard, e.g., a laminated cardboard. The strip 1 is advanced in the maker M1 along an elongated path (denoted in FIG. 1 by an arrow A) toward and through a material removing device 25 which provides longitudinally spaced-apart portions of the running strip 1 with transversely extending rows of substantially hourglass-shaped webs 2. Such webs are formed by making in the strip 1 transversely extending rows of cutouts 3 which alternate with the webs 2 of the respective rows and can constitute or resemble diamonds (squares or rectangles) or have an elliptical or even a circular outline. The strip 1 then reaches a draping station where it is converted into a substantially cylindrical envelope 4. The conversion of strip 1 into the envelope 4 involves the application of a suitable adhesive (e.g., a hot melt) to at least one longitudinally extending marginal portion (e.g., 1a) of the strip at an adhesive applying station 17 and bonding of the one marginal portion 1a to the other longitudinally extending marginal portion 1b of the strip 1 at a bonding station 18 so that the overlapping marginal portions 1a and 1b form a longitudinally extending seam 19 which is parallel or nearly parallel to the axis of the envelope 4. The seam 19 is preferably ironed at a station 20 so that the outer marginal portion 1a of the seam does not extend outwardly beyond the adjacent portion of the envelope 4, i.e., that the outer side of the marginal portion 1a merges gradually into the outer side of the adjacent longitudinally extending portion of the envelope 4.

The envelope 4 is thereupon severed at regular intervals at a severing station 5 in such a way that cuts are made substantially or exactly midway across the central portions of the rows of webs 2 whereby each web 2 yields two substantially triangular petals 6 and the petals 6 form sets 7 of projections at both ends of each of the thus obtained tubes 8. Successive tubes 8 are thereupon shifted sideways (arrow B in FIG. 1) to advance toward, through and beyond a cutting station 9 where a knife or a set of knives severs the tube 8 midway between its ends so that each tube 8 yields a pair of tubular sections 10 each having a set 7 of petals 6 at one of its ends. One section 10 of each pair of sections is thereupon turned end-for-end so that its set 7 of petals 6 faces in the same direction as the set of petals on the non-inverted section 10, and such sections are transferred into a maker or assembler M3 of applicators 11 wherein they receive tampons 12 as well as portions of pushers or plungers 26. The pushers 26 preferably constitute tubes with open ends so that the customary pull threads 27 can pass therethrough in order to facilitate extraction of tampons 12 from body cavities.

In accordance with a presently preferred embodiment of the invention, tubular sections 10 constitute the outer tubular components of twin-walled sleeves 110 each of which further comprises an inner tubular component 16. Each component 16 constitutes approximately or exactly one-half of a tubular reinforcing member 15 which is formed in a maker M2 (shown in FIGS. 1, 4 and 7) in the following way:

A supply (e.g., a bobbin 28) of a second strip 21 (the material of this strip can but need not be identical with the material of the strip 1) is advanced along a path which is indicated by the arrow C and is converted into a continuous envelope 22, e.g., in the same way as described in connection with the making of the envelope 4. The envelope 22 is cut at regular intervals at a severing station 23 so as to yield a series of tubular reinforcing members 15 which are moved sideways (arrow D) to a juxtaposing station 14 in the maker M1. Each reinforcing member 15 is juxtaposed with the adjacent portion of the running strip 1 in such a way that it is located between two successive sets 7 of petals 6, and more particularly between two successive rows of webs 2 as shown in the middle of FIG. 1. Thus, the juxtaposition of reinforcing members 15 with the strip 1 takes place prior to conversion of the strip into the envelope 4 and in such a way that the reinforcing members are confined in the envelope. The mutual spacing of the rows of webs 2 and the lengths of reinforcing members 15 are selected in such a way that the ends of the reinforcing members do not (or do not appreciably) overlap the adjacent webs 2, i.e., the petals 6 of tubes 8 which are formed at the severing station 5 extend axially of the tubes beyond the respective ends of the reinforcing members 15.

Each reinforcing member 15 is severed at the cutting station 9, together with the respective tube 8, so that it yields two shorter reinforcing members each of which constitutes the inner component 16 of the respective twin-walled sleeve 110.

The doming of sets 7 of petals 6 takes place in the maker M3. Each petal 6 is converted into a portion 6' of a hollow bullet-shaped crown 7' (FIG. 2) which at least substantially closes the respective end of the sleeve 110. Such conversion of petals 6 into domed petals 6' can take place prior or subsequent to insertion of tampons 12 which can be inserted through that end of the sleeve which is defined by the petals 6 or through the other end.

The maker M3 or the maker M1 preferably provides the petal-free end of each sleeve 110 with a set of inwardly extending indentations 13 which can form two or more axially spaced-apart annuli (see FIG. 2) and serve to center the adjacent end portion of the pusher 26. As shown in FIG. 5, the extent to which the indentations 13 project into the interior of the sleeve 110 is or can be such that the outer diameter of the preferably tubular pusher 26 is considerably less than the inner diameter of the sleeve 110. This not only results in considerable savings in material but also ensures that the front end face of the pusher 26 engages the adjacent rear end of the tampon 12 at a location inwardly of the internal surface of the sleeve 110 (i.e., at a location which is spaced apart from the internal surface of the inner tubular component 16 of such sleeve). Thus, the front end of the pusher 26 is less likely to clamp some material of the tampon 12 against the internal surface of the sleeve 110; this could necessitate the application of a substantial force in order to open the domed petals 6' during expulsion or attempted expulsion of the tampon 12 from the sleeve 110. Still further, the provision of centering indentations 13 reduces the area of frictional engagement between the sleeve 110 and the pusher 26 so that the tampon 12 can be expelled with the exertion of a relatively small force.

The indentations 13 can be made subsequent to insertion of the front end portion of the pusher 26 into the respective end of the sleeve 110, and the depth of these indentations can be selected with a view to ensure adequate centering of the pusher in the sleeve as well as to establish a desirable frictional engagement between the surfaces bounding the indentations 13 in the interior of the sleeve and the adjacent portions of the external surface of the pusher. It will be seen that the provision of indentations 13 reduces the area of contact between the pusher 26 and the sleeve 110 from a large surface-to-surface contact substantially to a mere line-to-line or point-to-point contact. If the indentations 13 are round or oval depressions in the outer side of the rear end of the sleeve 110, they preferably form two or more rows in order to ensure that the pusher 26 is centered in such a way that it cannot be readily tilted relative to the sleeve. This reduces the likelihood of malfunctioning of the applicator 11 preparatory to or during expulsion of the tampon 12.

The provision of indentations 13 entails a roughening of the outer side of the respective end of the sleeve 110 so that the sleeve can be more readily held by the user during advancement of the pusher 26 into the sleeve toward the crown 7' in order to expel the tampon 12 by way of the opening which is formed in response to outward flexing of domed petals 6' from the positions shown in FIG. 2 to the positions shown in FIG. 1. it is clear that the exterior of the sleeve 110 can be roughened (by ribs, other serrations, grooves or the like) in addition to the provision of indentations 13.

The making of cutouts 3 and webs 2 at the respective station in the maker M1 is carried out with a view to ensure that the tubes 8 are formed with sets 7 of uniformly distributed petals 6. This can be achieved by distributing the cutouts 3 in such a way that the narrowest (central) portions of the two outermost webs 2 are spaced apart from the respective marginal portions 1a, 1b of the strip 1 or that the two outermost webs 2 of each row accurately overlie each other upon completion of the bonding operation at the station 18. The first mentioned mode of distributing the webs 2 is preferred because the flexibility of all petals 6 is then the same.

An important advantage of the improved method and apparatus is that the tubes 8 and the reinforcing members 15 (or at least the tubes 8) are not or need not be made by helically winding one or more strips of paper or the like. This renders it possible to make the cutouts 3 in a running strip (1) of suitable deformable material rather than upon completed conversion of one or more strips into a tubular envelope and subdivision of the envelope into discrete tubes as is the rule in connection with the making of certain types of presently known tampon applicators.

Another important advantage of the improved method and apparatus is that the petals 6 need not be made in all layers of a sleeve 110 if the sleeve comprises several coaxial tubular components (10 and 16). This ensures that the petals 6 can be readily domed as well as that the domed petals 6' can more readily move apart to provide room for expulsion of the tampon 12.

The making of serrations in the ends of tubes which are formed by subdividing an envelope which is obtained from a helically convoluted strip of paper or the like in order to form sets of petals often results in so-called flake-off of smaller or larger particles of petals which then remain in the body cavity upon completed insertion of the tampon and can cause discomfort or even infection. All this is avoided by making the envelope 4 from a strip 1 in such a way that the envelope exhibits a longitudinally extending seam 19 which is parallel to the axis of the envelope. Moreover, the making of petals 6 is simplified by the expedient of forming the cutouts 3 in the running strip 1 rather than by serrating or notching the axial ends of discrete tubes.

FIG. 3 shows a modified applicator 11A which differs from the applicator 11 of FIG. 2 in that the rear end of the sleeve 110A is indented and deformed in a different way so as to form four substantially axially parallel ribs 13B alternating with indentations 13A to center the pusher 26A. In all other respects, the applicator 11A is or can be identical with the applicator 11 of FIG. 2.

Figure 4:
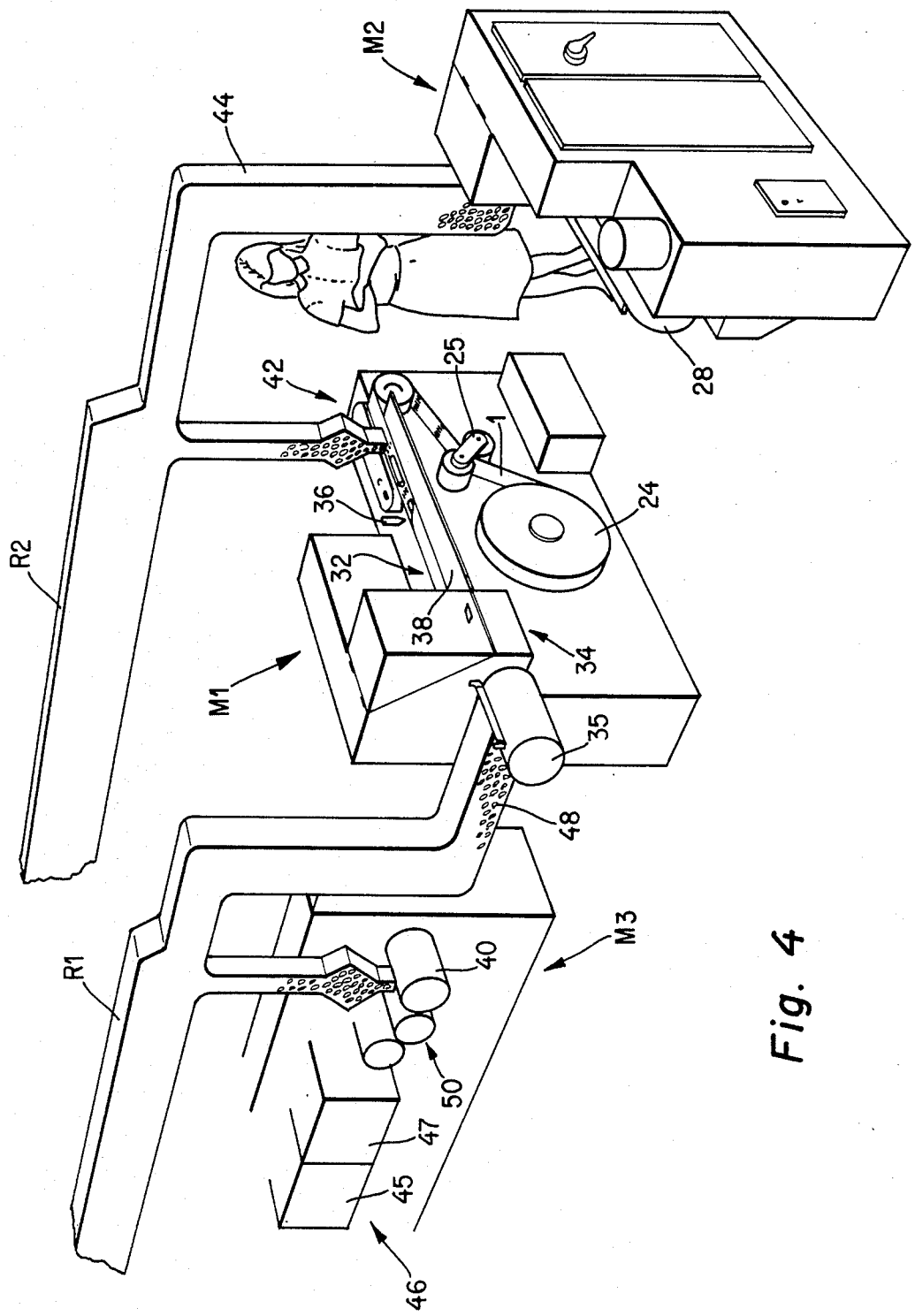
FIG. 4 is a partly schematic perspective view of an apparatus which can be used to make applicators of the type shown in FIGS. 2 or 3.

One presently preferred form of apparatus for making applicators 11 or 11A is shown in FIG. 4. This apparatus comprises the maker M1 which turns out tubes 8 and discharges the tubes into the inlet of a duct 48 constituting a means for transferring tubes to the maker M3, namely to a cutting drum 40 which subdivides each tube 8 into two shorter tubular sections 10. The duct 48 communicates with the combined inlet and outlet of a first-in last-out reservoir R1 which serves to store the surplus of tubes 8 when the output of the maker M1 exceeds the requirements of the means (46) for inserting tampons 12 into the sleeves 110 in the maker M3, and to deliver tubes 8 into the duct 48 when the requirements of the inserting means 46 exceed the output of the maker M1 (e.g., when the maker M1 is idle due to malfunctioning of one of its aggregates or for another reason).

The maker M1 comprises the aforementioned source 24 of supply of the strip 1 and the aforementioned material removing device 25 which serves to remove material from the running strip 1 and to thus form the cutouts 3 and webs 2. The removing device 25 can comprise an orbiting knife at one side and an anvil at the other side of the respective portion of the path for the strip 1. The exact details of the device 25 (save for the feature that it can provide the running strip 1 with substantially hourglass-shaped webs 2) forms no part of the present invention. The peripheral speed of the rotary parts of the material removing device 25 matches or closely approximates the speed of the strip 1.

The maker M1 further comprises a suitable adhesive applicator 36 (e.g., a nozzle connected to a source of pressurized adhesive) which is disposed at the station 17 and provides the marginal portion 1a of the strip 1 with a film of adhesive which is used to bond the marginal portion 1a to the marginal portion 1b at the bonding station 18 defined by a converting unit 32 of the maker M1. The converting unit 32 is or can be similar to the wrapping mechanism of a cigarette maker, e.g., a machine known as PROTOS which is manufactured by Hauni of Hamburg, German Federal Republic. The unit 32 comprises means for converting the strip 1 first into a substantially channel-shaped body having a U-shaped cross-sectional outline prior to application of adhesive film by the applicator 36 and for thereupon bonding the marginal portions 1a, 1b of the strip 1 to each other so that the channel-shaped body is converted into the aforementioned tubular envelope 4. The seam 19 of the envelope 4 is heated or cooled (depending on the nature of adhesive which is applied to the marginal portion 1a) by a bonding device 38 which can also comprise or constitute the means for ironing the seam 19 so as to ensure that the outer side of the outer marginal portion 1a merges gradually into the outer side of the adjacent longitudinally extending portion of the envelope 4. The bonding device 38 is shown schematically in FIG. 6; it comprises a steel core 38a which extends into the interior of the envelope 4 and a sealer 38b which is adjacent to the outer side of the seam 19 and deforms the seam as shown so as to ensure that the external surface of the envelope 4 is or resembles a circular cylinder.

The bonding device 38 is followed by a cutoff 34 which severs the envelope 4 at the station 5 so that each row of webs 2 yields two sets 7 of petals 6 in a manner as described in connection with FIG. 1.

The cutoff 34 is followed by a drum 35 which changes the direction of travel of tubes 8 (note the arrow B in FIG. 1) and directs the tubes 8 into the duct 48. The tubes 8 advance in the duct 48 toward and into the maker M3 and/or into the reservoir R1. This reservoir can be of the type known as RESY which is manufactured by Hauni of Hamburg, German Federal Republic. Reference may be had, for example, to U.S. Pat. No. 4,353,454 granted to Tolasch et al. Other types of reservoirs (e.g., of the type disclosed in U.S. Pat. No. 4,365,702 to Tolasch et al.) can be used with equal or similar advantage.

The discharge end of the duct 48 delivers tubes into successive axially parallel peripheral flutes of the rotary cutting drum 40 which is located at the station 9 and subdivides each tube 8 into a pair of tubular sections 10. A suitable cutting drum is disclosed, for example, in U.S. Pat. No. 4,063,480 to Hinzmann. One section 10 of each pair is turned or inverted end-for-end in a turnaround device 50 of the type disclosed, for example, in U.S. Pat. No. 4,154,090 to Heitmann et al. so that the petals 7 of all sections 10 face in the same direction before the sections 10 enter the inserting means 46. The exact manner of inserting tampons 12 into the sections 10 and of inserting the pushes 26 forms no part of the present invention. Reference may be had to the aforementioned U.S. Pat. Nos. 4,302,174 and 4,321,993 and to the machine known as HP 400 which is built by the assignee of the present application. The inserting means 46 comprises means 47 for providing the sleeves 110 with indentations 13 and with means 45 for doming the petals 6 so as to form the aforediscussed crowns 7'. Finished applicators 11 are transported to a packing machine PM (FIG. 7) and/or into a further reservoir R4 which may but need not be a first-in first-out reservoir.

The maker M2 of FIG. 4 comprises the bobbin 28 or another suitable source of supply of strip 21 which is treated in the same way as the strip 1 (in the maker M1) except that the strip 21 is not formed with cutouts and webs. The reinforcing members 15 which advance beyond the severing station 23 in the maker M2 enter the inlet of a transferring device 44 in the form of a duct serving to deliver reinforcing members 15 to juxtaposing device 42 at the juxtaposing station 14 of the maker M1 and/or into the inlet-outlet of a further first-in last-out reservoir R2. The latter receives reinforcing members 15 when the output of the maker M2 exceeds the requirements of the maker M1, and discharges reinforcing members 15 into the duct 44 when the requirements of the maker M1 at the juxtaposing station 14 exceed the output of the maker M2. The juxtaposing device 42 can comprise an endless belt conveyor (shown in FIG. 4) with entraining elements which advance successive reinforcing members 15, issuing from the duct 44, in the direction of arrow A so as to accelerate the reinforcing members to the exact speed of the strip 1 as well as to deposit each reinforcing member midway between the preceding and next-following rows of webs 2.

Figure 7:
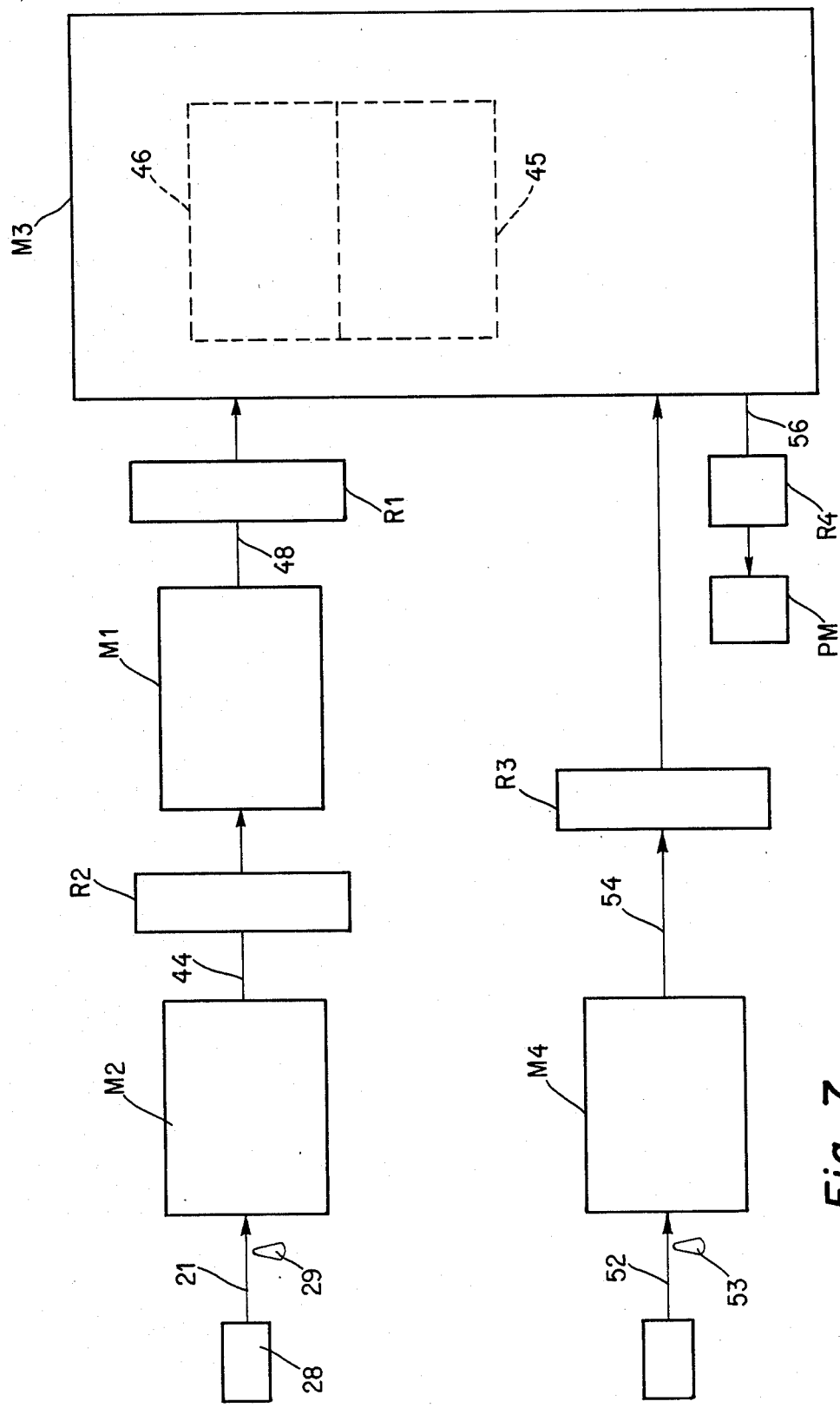
FIG. 7 is a diagrammatic plan view of a complete apparatus which makes reinforcing members, shells and plungers and assembles such parts into applicators.

Referring finally to FIG. 7, there is shown an entire apparatus which includes the aforementioned maker M2 of reinforcing members 15, the strip 21 which comes from the source 28 and is provided with a film of adhesive at 29, and the duct 44 which leads to the reservoir R2 as well as to the maker M1. The maker M1 admits tubes 8 into the duct 48 which delivers the tubes into the reservoir R1 and/or into the maker M3.

The apparatus further comprises a maker M4 which turns out pushers 26 and which can be similar to or identical with the maker M2. A marginal portion of the strip 52 which is converted into pushers 26 in the maker M4 is coated with a film of adhesive at 53 and the maker M4 admits pushers 26 into a duct 54 for delivery to the maker M3 and/or to a reservoir R3 which is or can be identical with the reservoir R1 and/or R2 and/or R4. The reservoir R4 can cooperate with a transferring unit 56 which extends between the outlet of the maker M3 and the packing machine PM.

The maker M4 and/or M2 can be designed to make pushers 26 and/or reinforcing members 15 from a spirally wound laminated paper tube. A rudimentary apparatus for making such tubes is disclosed in U.S. Pat. No. 1,006,976, and another apparatus for making tubes from spirally wound strips of paper or the like is disclosed in German Offenlegungsschrift No. 35 18 831.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A method of making tubes, particularly for use in applicators of catamenial tampon pledgets, comprising the steps of conveying a strip of degradable material longitudinally along a predetermined path; removing material from longitudinally spaced-apart portions of the strip in a first portion of the path so as to form transversely extending rows of substantially hourglass-shaped webs; converting the strip into a tubular envelope in a second portion of the path; and severing the envelope substantially midway across the rows of webs in a third portion of the path so as to subdivide the envelope into a series of tubes having open ends formed by circumferentially extending sets of petals, each set being configurated so as to be formable into a crown in the region of an end of an inserted pledget, with each petal constituting approximately one-half of a web.

2. The method of claim 1, further comprising the step of storing at least some tubes of said series in a first-in last-out reservoir.

3. The method of claim 1, further comprising the step of cutting each tube substantially midway between its ends to form pairs of tubular sections each having two open ends and a set of petals at one of its ends.

4. The method of claim 3, further comprising the step of providing each tubular section with inwardly extending indentations in the region of the other end of the tubular section.

5. The method of claim 3, further comprising the step of doming the sets of petals so that such petals form substantially bullet-shaped crowns which close the respective ends of the tubular sections.

6. The method of claim 1, further comprising the step of juxtaposing successive discrete tubular reinforcing members with the strip so that each reinforcing member is located between two successive rows of webs not later than upon arrival of the webs into the second portion of the path and the reinforcing members are confined in the envelope in the course of the converting step.

7. The method of claim 6, further comprising the step of cutting the tubes and the respective reinforcing members substantially midway between their ends so that each tube and the respective reinforcing member yields two twin-walled sleeves each having an inner tubular component constituting substantially one-half of the respective reinforcing member and an outer tubular component constituting substantially one-half of the respective tube and having a set of petals at one end thereof with the petals extending beyond the respective end of the inner component.

8. The method of claim 7, further comprising the step of storing at least some of the sleeves in a reservoir.

9. The method of claim 1, wherein said converting step includes applying adhesive to at least one longitudinally extending marginal portion of the strip and bonding the one marginal portion to the other longitudinally extending marginal portion of the strip so that the two marginal portions form a seam extending in substantial parallelism with the axis of the envelope.

10. The method of claim 9, further comprising the step of ironing the seam so as to provide a smooth transition between the exposed side of the outer marginal portion of the seam into the outer side of the adjacent longitudinally extending portion of the envelope.

11. The method of claim 1, wherein the degradable material is selected from the group consisting of paper, board, cardboard and paperboard.

12. Apparatus for making tubes, particularly for use in applicators of catamenial tampon pledgets, comprising a source of supply of a continuous strip of degradable material; means for advancing the strip from said source longitudinally along a predetermined path; means for removing material from longitudinally spaced-apart portions of the strip in a first portion of the path so as to form transversely extending rows of substantially hourglass-shaped webs; means for converting the strip into a tubular envelope in a second portion of the path; and means for severing the envelope substantially midway across successive rows of webs so as to subdivide the envelope into a series of tubes each of which has open ends formed by circumferentially extending sets of petals, each set being configurated so as to be formable into a crown in the region of an end of an inserted pledget, with each petal constituting approximately one-half of a web.

13. The apparatus of claim 12, wherein said converting means comprises means for applying adhesive to at least one longitudinally extending marginal portion of the strip and means for bonding the one marginal portion to the other longitudinally extending marginal portion of the strip so as to form a seam which extends in substantial parallelism with the axis of the envelope.

14. The apparatus of claim 13, wherein said converting means further comprises means for ironing the seam so as to provide a smooth transition between the exposed side of the outer marginal portion of the seam and the outer side of the adjacent longitudinally extending portion of the envelope.

15. The apparatus of claim 12, further comprising means for cutting the tubes substantially midway between their ends so that each tube yields two tubular sections each having a set of petals at one of its ends.

16. The apparatus of claim 12, further comprising a source of tubular reinforcing members and means for juxtaposing discrete reinforcing members with the strip between said source of supply and said converting means in such distribution that each reinforcing member is disposed between two consecutive rows of webs and the reinforcing members are confined in the envelope which is formed by said converting means so that each tube contains a reinforcing member and the sets of petals of each tube extend beyond the respective ends of the reinforcing member therewithin.

17. The apparatus of claim 16, further comprising means for cutting the tubes and the respective reinforcing members substantially midway between their ends to form twin-walled sleeves each having an inner tubular component constituting substantially one-half of the respective reinforcing member and an outer tubular component constituting substantially one-half of the respective tube and having a set of petals at one end thereof with the petals extending beyond the respective end of the inner component.

18. The apparatus of claim 16, wherein said source of reinforcing members includes a maker of reinforcing members, means for transferring reinforcing members from said maker to said juxtaposing means, and a reservoir communicating with said transferring means to receive the surplus of reinforcing members when the maker supplies reinforcing members at a rate exceeding the requirements of the juxtaposing means and to supply reinforcing members to said transferring means when the requirements of said juxtaposing means exceed the output of the maker.

19. The apparatus of claim 12, further comprising means for cutting the tubes substantially midway between their ends so that each tube yields two tubular sections each having a set of petals at one of its ends, means for inserting pledgets into the sections, and means for transferring sections from said cutting means to said inserting means.

20. The apparatus of claim 12, further comprising means for inserting pledgets, means for transporting tubes from said severing means toward said inserting means, and a reservoir connected with said transporting means to receive tubes when the rate at which the tubes are formed exceeds the requirements of the inserting means and to supply stored tubes to the transporting means when the requirements of the inserting means exceed the rate of making the tubes.

* * * * *